(12) United States Patent
McLeay

(10) Patent No.: US 11,446,244 B2
(45) Date of Patent: Sep. 20, 2022

(54) COMPOSITIONS CONTAINING VERTEPORFIN, RIBAVIRIN, GEMCITABINE, OR COMBINATIONS THEREOF AND METHODS OF USE FOR TREATING COVID-19, CANCER, OR NON CANCER DISEASES

(71) Applicant: Matthew McLeay, Omaha, NE (US)

(72) Inventor: Matthew McLeay, Omaha, NE (US)

( * ) Notice: Subject to any disclaimer, the term of this patent is extended or adjusted under 35 U.S.C. 154(b) by 0 days.

(21) Appl. No.: 17/151,191

(22) Filed: Jan. 17, 2021

(65) Prior Publication Data

US 2021/0220265 A1  Jul. 22, 2021

Related U.S. Application Data

(60) Provisional application No. 62/962,382, filed on Jan. 17, 2020, provisional application No. 62/967,777, filed on Jan. 30, 2020.

(51) Int. Cl.

| | |
|---|---|
| *A61K 9/00* | (2006.01) |
| *A61K 31/02* | (2006.01) |
| *A61K 31/197* | (2006.01) |
| *A61K 31/198* | (2006.01) |
| *A61K 31/409* | (2006.01) |
| *A61K 31/7056* | (2006.01) |
| *A61K 31/7068* | (2006.01) |
| *A61K 31/728* | (2006.01) |
| *A61K 45/06* | (2006.01) |
| *A61K 47/26* | (2006.01) |
| *A61P 31/14* | (2006.01) |
| *A61P 35/04* | (2006.01) |

(52) U.S. Cl.
CPC .......... *A61K 9/0075* (2013.01); *A61K 9/0043* (2013.01); *A61K 9/0078* (2013.01); *A61K 31/02* (2013.01); *A61K 31/197* (2013.01); *A61K 31/198* (2013.01); *A61K 31/409* (2013.01); *A61K 31/7056* (2013.01); *A61K 31/7068* (2013.01); *A61K 31/728* (2013.01); *A61K 45/06* (2013.01); *A61K 47/26* (2013.01); *A61P 31/14* (2018.01); *A61P 35/04* (2018.01)

(58) Field of Classification Search
None
See application file for complete search history.

(56) References Cited

U.S. PATENT DOCUMENTS

| | | | | |
|---|---|---|---|---|
| 6,136,346 | A * | 10/2000 | Eljamal | A61K 9/0075 424/488 |
| 9,925,144 | B2 * | 3/2018 | Fabio | A61K 9/1617 |
| 10,874,687 | B1 | 12/2020 | Sommadossi et al. | |
| 2006/0159658 | A1 * | 7/2006 | Deo | A61P 35/00 424/85.7 |
| 2007/0117788 | A1 * | 5/2007 | Yeadon | A61P 11/06 514/211.13 |
| 2010/0297033 | A1 * | 11/2010 | McLeay | A61K 38/446 424/45 |
| 2011/0048420 | A1 * | 3/2011 | Gibbins | A61M 15/0036 128/203.21 |
| 2011/0056492 | A1 * | 3/2011 | Longest | A61M 11/042 128/203.15 |
| 2014/0190496 | A1 * | 7/2014 | Wensley | A24B 15/167 131/273 |
| 2018/0369513 | A1 * | 12/2018 | Hannon | A61M 15/0008 |
| 2020/0215065 | A1 * | 7/2020 | Irwin | A61K 47/06 |
| 2020/0368263 | A1 | 11/2020 | Dempsey et al. | |
| 2020/0368297 | A1 * | 11/2020 | Chen | A61K 35/747 |
| 2021/0040135 | A1 * | 2/2021 | Kim | C07H 19/06 |
| 2021/0069098 | A1 | 3/2021 | Mcleay | |
| 2021/0196776 | A1 * | 7/2021 | Cho | A61K 36/258 |

(Continued)

FOREIGN PATENT DOCUMENTS

| | | | |
|---|---|---|---|
| CN | 106551909 A | * | 4/2017 |
| CN | 106551909 A | | 4/2017 |
| WO | 2017085692 A1 | | 5/2017 |

(Continued)

OTHER PUBLICATIONS

DERWENT abstract for CN 106551909A (2017).*

(Continued)

*Primary Examiner* — Sin J Lee
(74) *Attorney, Agent, or Firm* — Kutak Rock LLP

(57) ABSTRACT

Disclosed are pharmaceutical formulations and methods using Verteporfin Ribavirin and/or Gemcitabine for use in the treatment of diseases by various routes of administration including inhalation, intratumoral, topical and/or systemic injection administration. This invention relates more specifically to the use of Verteporfin, Ribavirin, Gemcitabine, and/or combinations thereof as an inhaled dry powder treatment for COVID-19 and/or other lung infections, cancer and other non-cancer applications, which may be followed by other treatment regimens including radiation therapy, photodynamic therapy, and/or sonodynamic therapy. These pharmaceutical compositions containing one or more of Verteporfin, Ribavirin, and Gemcitabine may be included in pharmaceutical kits containing the compositions, and to methods for the treatment of cancer and non-cancer diseases with the active agents of the pharmaceutical compositions. The administering of Verteporfin alone or in combination with Ribavirin and Gemcitabine may be followed or co-administered with photodynamic and/or sonodynamic therapy (PDT/SDT).

16 Claims, No Drawings

(56) References Cited

U.S. PATENT DOCUMENTS

2021/0228485 A1    7/2021    Mcleay

FOREIGN PATENT DOCUMENTS

| WO | WO-2019104038 A1 * | 5/2019 | ................ A61P 9/10 |
| WO | 2021154687 A1 | 8/2021 | |

OTHER PUBLICATIONS

Machine-assisted English translation for CN 106551909A (2017).*
Respaud et al ("Effect of formulation on the stability and aerosol performance of a nebulized antibody", mAbs, 6:5, p. 1347-1355 (2014), obtained online from the website: https://www.tandfonline.com/doi/pdf/10.4161/mabs.29938). (Year: 2014).*
Dumont et al., A Novel Inhaled Dry-Powder Formulation of Ribavirin Allows for Efficient Lung Delivery in Healthy Participants and Those with Chronic Obstructive Pulmonary Disease in a Phase 1 Study, Antimicrobial Agents and Chemotherapy, May 2020, pp. 1-15, vol. 64, issue 5.
Wong et al., Clinical outcomes of different therapeutic options for COVID-19 in two Chinese case cohorts: A propensity-score analysis, pp. 1-13, EClinicalMedicine 32 (2021).
Ferron et al., Structural and molecular basis of mismatch correction and ribavirin excision from coronavirus RNA, PNAS, Dec. 26, 2017, pp. E162-E171.
Gilbert and McLeay, MegaRibavirin Aerosol for the Treatment of Influenza A Virus Infections in Mice, Antiviral Res., Jun. 2008, pp. 223-229, vol. 78, issue 3.
Govorkova and Webster, Combination Chemotherapy for Influenza, Viruses, pp. 1510-1529, 2010, 2.
Li et al., Potential antiviral therapeutics for 2019 Novel Coronavirus, PubMed, Mar. 12, 2020, pp. 170-172, vol. 43 issue 3.
Liu et al., Efficacy and safety of antiviral treatment for COVID-19 from evidence in studies of SARS-CoV-2 and other acute viral infections: a systematic review and meta-analysis, CMAJ, Jul. 6, 2020, pp. E734-E744, vol. 192, issue 27.
Martinez, Miguel Angel, Compounds with Therapeutic Potential against Novel Respiratory 2019 Coronavirus, May 2020, pp. 1-7, vol. 64, issue 5.
Tong et al., Ribavirin therapy for severe COVID-19: a retrospective cohort study, International Journal of Antimicrobial Agents, 2020, vol. 56.
Barnard et al., Enhancement of the infectivity of SARS-CoV in BALB/c mice by IMP dehydrogenase inhibitors, ncluding ribavirin, Antiviral Research, 2006, pp. 53-63, vol. 71.
"Non- Final Action received for U.S. Appl. No. 17/231,735, dated Sep. 22, 2021".
Renard, Sebastien MD, et al., Severe Pulmonary Arterial Hypertension in Patients Treated for Hepatitis C With Sofosbuvir, 2016 149(3):e69-e73 Chest.
Highlights of Prescribing Information for Copegus (ribavirin) Tablets; Revised Aug. 2011, Genentech, Inc.
Bliss, Susan J., "Ribavirin: Understanding the Long-Term Side Effects"; Aug. 15, 2018, p. 1-12.
"Non-Final Action received for U.S. Appl. No. 17/231,735, dated May 27, 2021".
"Final Office Action Received for U.S. Appl. No. 17/231,735, dated Feb. 9, 2022."
Messina, Emanuela , et al., ""Ribavirin Aerosol in the Treatment of SARS-CoV-2: A Case Series", Infect Dis Ther (2021) 10:2791-2804".

* cited by examiner

COMPOSITIONS CONTAINING VERTEPORFIN, RIBAVIRIN, GEMCITABINE, OR COMBINATIONS THEREOF AND METHODS OF USE FOR TREATING COVID-19, CANCER, OR NON CANCER DISEASES

CROSS-REFERENCE TO RELATED APPLICATIONS

This application claims the benefit of U.S. Ser. No. 62/967,777, filed Jan. 30, 2020, and U.S. Ser. No. 62/962,382, filed Jan. 17, 2020, each of which is herein incorporated by reference in its entirety.

FIELD

This invention relates to pharmaceutical formulations and methods using Verteporfin Ribavirin and/or Gemcitabine for use in the treatment of diseases by various routes of administration including inhalation, intratumoral, topical and/or systemic injection administration. This invention relates more specifically to the use of Verteporfin, Ribavirin, Gemcitabine, and/or combinations thereof as an inhaled dry powder treatment for COVID-19 and/or other lung infections, cancer and other non-cancer applications, which may be combined with other therapies such as photodynamic therapy and/or sonodynamic therapy.

BACKGROUND

There remains a significant unmet medical need for both cancer and high morbidity and mortality conditions for both human and companion animals including, among other indications, lung cancer and COVID-19. The COVID-19 pandemic has created an urgent need for rapid and easy to administer therapies, especially therapies designed to be given early and relatively soon after infection or the onset of symptoms. The applicant has discovered that one or more known drugs, when administered via new formulations, combinations, administration schedules, routes of administration, or with companion therapy regimens, are effective in treating COVID-19 as well as other diseases, including cancer.

The drug Verteporfin, a benzoporphyrin derivative, has been found to be an excellent photodynamic therapy (PDT) agent. Verteporfin also possesses potential anti-cancer and anti-inflammatory properties that might be exploited to provide comfort to those patients in need. Currently, liposomal Verteporfin is used for PDT in age related macular degeneration and has been approved by the USFDA since 2000.

The drug Ribavirin is a nucleoside analogue and has been approved for use in a nebulizer to treat respiratory syncytial virus (RSV) infections. Its use in treating COVID-19 is not expected by skilled pulmonologists and infectious disease specialists to be successful in treating COVID-19.

For example, Wang et al ("Potential antiviral therapeutics for 2019 Novel Coronavirus," 2020 Mar. 12; 43(3):170-172. Chinese. doi: 10.3760/cma.j.issn.1001-0939.2020.03.004. PMID: 32164080.1) have concluded that some "[a]ntiviral drugs commonly used in clinical practice, including neuraminidase inhibitors (oseltamivir, paramivir, zanamivir, etc.), ganciclovir, acyclovir and Ribavirin, are invalid for 2019-nCoV and not recommended." Wang, 2020, at abstract.

Liu et al. ("Efficacy and safety of antiviral treatment for COVID-19 from evidence in studies of SARS-CoV-2 and other acute viral infections: a systematic review and meta-analysis," CMAJ Jul. 6, 2020 192 (27) E734-E744; DOI: https://doi.org/10.1503/cmaj.200647) have concluded that "[b]oth SARS and MERS studies provided very low-quality evidence for effects of treatment using Ribavirin on mortality in patients with severe COVID-19 illness," Liu, 2020, at p. E737, col. 2.

Barnard et al. ("Enhancement of the infectivity of SARS-CoV in BALB/c mice by IMP dehydrogenase inhibitors, including Ribavirin," Antiviral Res. 2006 August; 71(1): 53-63) have concluded, based on results showing increased SARS-CoV1 infection in mice treated with Ribavirin, that "using Ribavirin as therapy for treating SARS infections should be reconsidered," Barnard, 2006, at p. 62, col. 1.

Ferron et al. ("Structural and molecular basis of mismatch correction and Ribavirin excision from coronavirus RNA," Proc Natl Acad Sci USA, 2018 Jan. 9; 115(2):E162-E171. doi: 10.1073/pnas.1718806115. Epub 2017 Dec. 26) have concluded that endogenous "exonuclease activity of nsp14 can efficiently excise the nucleoside analog chain terminator Ribavirin" thereby rendering this antiviral drug of no use against Coronaviruses, and "coronavirus (CoV)-infected patients do not respond to [Ribavirin]," Ferron, 2018, at p. E161, col. 1.

Tong et al. ("Ribavirin therapy for severe COVID-19: a retrospective cohort study. Int J Antimicrob Agents. 2020 September; 56(3):106114. doi: 10.1016/j.ijantimicag.2020.106114. Epub 2020 Jul. 23. PMID: 32712334; PMCID: PMC7377772) have concluded that "in patients with severe COVID-19, Ribavirin therapy is not associated with improved negative conversion time for SARS-CoV-2 test and is not associated with an improved mortality rate," Tong, 2020, at abstract.

Miguel Angel Martinez ("Compounds with Therapeutic Potential against Novel Respiratory 2019 Coronavirus," Antimicrob Agents Chemother. 2020 May; 64(5): e00399-20) has concluded that "Ribavirin reduces hemoglobin concentrations, an undesirable side effect in patients with respiratory disorders[, which] . . . reduces [Ribavirin's] potential as an antiviral against SARS-CoV-2," Martinez, 2020, at p. 4, para. 3.

Tonga et al. ("Ribavirin therapy for severe COVID-19: a retrospective cohort study," International Journal of Antimicrobial Agents, Volume 56, Issue 3, September 2020, 106114) conclude from examining patients that had received intravenous Ribavirin versus supportive care only that "Ribavirin was not associated with reduced negative conversion time of SARS-CoV-2 PCR test compared with the control group [and that] Ribavirin did not reduce the mortality rate compared with the control group," Tonga, 2020, at highlights.

The drug Gemcitabine, another nucleoside analog, is approved for intravenous administration to treat cancer. However, Gemcitabine carries a warning label that it can suppress bone marrow function and may cause capillary leak syndrome and severe lung conditions like pulmonary edema, pneumonia, and adult respiratory distress syndrome. Thus, the ordinarily skilled pulmonologist would not expect Gemcitabine to be effective against lung infections, especially SARS-inducing COVID-19.

Despite the lack of any expectation of success in using any of Ribavirin, Verteporfin, and Gemcitabine, applicant has discovered that any one of Ribavirin, Verteporfin, and Gemcitabine, or any combination thereof, delivered to the lungs of a COVID-19 infected patient, preferably soon after infection, such as within 72-hours of symptoms, will reduce viral load and prevent or reduce severe acquired respiratory syndrome in that patient.

Disclosed are pharmaceutical compositions containing Verteporfin, Ribavirin and Gemcitabine and methods of administering these products containing compositions in a convenient manner to a patient with cancer or a non-cancer hyperplastic or dysplastic disease, or other patient in need thereof. For Verteporfin, Photo and Sonodynamic Therapy are emphasized remedies alone or with Perflubron emulsion.

SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

Disclosed are a pharmaceutical composition, a mode of administration, and a method of treating lung infections or other lung diseases, especially COVID-19, but also including other ARDS, SARS, pneumonia, cancer, and non-cancer diseases by administering any one of or any combination of Verteporfin, Ribavirin, and Gemcitabine, preferably with one or more excipients. In some embodiments, the excipient is a stabilizer, a surfactant, a buffer, a rheological agent, or the like. In some embodiments, the excipient is a functional excipient, such as a perfluorocarbon, a bioactive amino acid or peptide, or the like.

Preferred embodiments describe the direct delivery to the lungs of a patient in need of any one or combination of Verteporfin, Ribavirin, and Gemcitabine. In some embodiments, direct delivery to the lungs means that the drug is delivered as an inhaled dry powder, dry aerosol particles, liquid aerosol particles, or the like, such as via a dry powder inhaler (DPI), a nebulizer, a metered dose inhaler (MDI), or the like.

Preferred patients-in-need include patients with a lung infection, such as a viral lung infection like influenza, COVID-19, or the like. Patients-in-need also include those patients with lung cancer or other lung diseases such as COPD or the like.

In some embodiments, the subject lung treatment also includes other steps or interventions. For example, in one embodiment, photodynamic therapy (e.g., delivering near infra-red electromagnetic waves to the diseased area) or sonodynamic therapy (e.g., delivering sound waves, preferably targeted to the diseased area) to promote cell killing, especially tumor cells. In another embodiment, the drugs may be delivered sequentially and/or in different forms or routes of administration such as intravenous, dry powder versus liquid aerosol, and the like, and Gemcitabine and/or Ribavirin followed by Verteporfin, Gemcitabine followed by Ribavirin and/or Verteporfin, Ribavirin, Ribavirin and/or Verteporfin followed by Gemcitabine, Gemcitabine and/or Ribavirin followed by Verteporfin, Verteporfin followed by Ribavirin and/or Gemcitabine, Gemcitabine followed by Verteporfin followed by Ribavirin, Gemcitabine followed by Ribavirin followed by Verteporfin, Gemcitabine followed by Verteporfin followed by Ribavirin, Ribavirin followed by Gemcitabine followed by Verteporfin, Ribavirin followed by Verteporfin followed by Gemcitabine, Verteporfin followed by Ribavirin followed by Gemcitabine, or Verteporfin followed by Gemcitabine followed by Ribavirin.

Many of the attendant features will be more readily appreciated as the same becomes better understood by reference to the following detailed description.

DETAILED DESCRIPTION

Disclosed are pharmaceutical formulations containing any one or more of Verteporfin, Ribavirin and Gemcitabine and optionally containing one or more pharmaceutically acceptable excipients. In one embodiment, the Verteporfin, Ribavirin and/or Gemcitabine-containing formulation is dry powder, a lyophilized cake or milled powder, a liquid or gel formulation for topical application, or an aerosolized liquid. In one embodiment, the liquid or gel is an emulsion or stable micellar suspension. In another embodiment, the liquid or gel is a solution.

Verteporfin is a hydrophobic molecule which is soluble in lipophilic solvents such as perfluorocarbons like perflubron. In an aqueous phase, Verteporfin forms an emulsion or micellar suspension. It is envisioned that a Verteporfin emulsion will be taken-up by tissues and cells much better than a hydrophilic drug, which often fails to be taken-up by diffusion. It is envisioned that the liposomal properties of the Verteporfin emulsion or suspension enable its binding to LDL receptors, which are found extensively on many malignant and nonmalignant tissues and cells, such as, e.g., atherosclerosis. Furthermore, the hydrophobic nature and concomitant tissue penetrability provides an additional advantage of deep light delivery compared to many other photosensitizers for photodynamic therapy (PDT). Additionally, this deep penetrability and cancer cell uptake enables the effective use of sonodynamic therapy (SDT), wherein the targeted sound waves trigger the excitation of electrons in the taken-up Verteporfin molecule and the presumed subsequent intersystem crossing and singlet oxygen/reactive oxygen species are produced and trigger tumor cell (or other cell) killing. Ribavirin dpi and Gemcitabine dpi will deliver to the lung epithelial lining fluid and enable diffusion into cancer cells and with reduced systemic side effects.

A topical formula (here topical may include mucosal as well as epidermal/dermal) containing one or more of Verteporfin, Ribavirin and/or Gemcitabine has significant advantages over an intravenous route to treat skin or other mucosal layer diseases including: reduced dosing because of direct interface with the affected tissue, no first pass metabolism through the liver or other organs, decreased side effects due to direct dosing at the site of the condition, improved imaging due to the higher concentration and improved tumor-to-background ratio possible by direct application, and the ease of repeat dosing.

In one embodiment, a liquid topical Verteporfin, Ribavirin and/or Gemcitabine-containing formulation may be administered by swishing the formulation in patient's buccal cavity, which would not require special equipment, a hospital or specialized care as is likely required for intravenous administration.

In one embodiment of a Verteporfin-containing formulation that forms a liposome, the liposomal formulation contains about 0.1 to 100 mg/mL Verteporfin, about 0.1-10 mg/mL, about 0.5-20 mg/mL, about 0.5-30 mg/mL, about 1-40 mg/mL, about 1-50 mg/mL, about 5-60 mg/mL, about 5-70 mg/mL, about 10-80 mg/mL, about 10-90 mg/mL, about 0.5 mg/mL, or about 100 mg/mL in a volume of about 5-50 mL, about 10-40 mL, about 15-30 mL, about 10 mL, about 20 mL, about 30 mL, about 40 mL, or about 50 mL.

In one embodiment, the liposomal formulation contains Verteporfin at a concentration of about 0.5 mg/ml in a volume of about 30 mL.

In another embodiment, the Verteporfin, Ribavirin, and/or Gemcitabine-containing formulation is a dry powder that can be administered via dry powder inhalation (DPI). Here, the Verteporfin, Ribavirin and/or Gemcitabine is/are readily absorbed into the systemic circulation of the patient without the need for intravenous administration. In some embodiments, a DPI formulation may also contain Aminolevulinate (ALA) alone or in combination with any one or more of the Verteporfin, Ribavirin and Gemcitabine. For example, dry powder Verteporfin, Ribavirin and Gemcitabine (and/or optionally, ALA) may be easily and repeatedly administered via DPI for treating inter alia and e.g., pancreatic cancer post PDT or atherosclerosis as compared to intravenous administration, which requires hospitalization or special equipment.

Furthermore, the small molecular weight and high hydrophobicity enables Verteporfin (and concomitantly those hydrophilic drugs—e.g., ALA, Gemcitabine, and Ribavirin—that are formulated/combined with the Verteporfin) to pass rapidly into the blood stream, bind lipoproteins, then travel to cancers and be taken up by LDL receptors (which are over-expressed in multiple tumors). Once in the disease tissue and cells, Verteporfin enables PDT and SDT as well as inhibits YAP1 (yes-associated protein 1) a suppressor of apoptotic gene expression and activator of cell proliferation genes, thus disrupting tumor cell and stromal cell function and survival.

In one embodiment, the dry powder formulation containing Verteporfin, Ribavirin and/or Gemcitabine (and/or optionally, ALA) contains >50% Verteporfin, Ribavirin, and/or Gemcitabine (i.e., the active agent) and one excipient. In one embodiment, the excipient is one or both of fumaryl diketopiperazine and a sugar alcohol such as, e.g., mannitol. In another embodiment, the dry powder formulation contains >96% Verteporfin, Ribavirin, and/or Gemcitabine (i.e., the active agent) and no more than 4% water.

In another embodiment, the Verteporfin, Ribavirin and/or Gemcitabine-containing formulation (for convenience, herein also referred to as "V-R-G active agent", which encompasses Verteporfin singly, Ribavirin singly, Gemcitabine singly, Verteporfin+Ribavirin, Verteporfin+Gemcitabine, Gemcitabine+Ribavirin, and Gemcitabine+Ribavirin+Verteporfin) is a dry powder that remains stable and therapeutically, physiologically, or biologically stable at room temperature for many months. The powder comprises a plurality of particles, most of which comprise V-R-G active agent, less than 6% (w/w) water, and additional ingredients that include a sugar and/or a sugar alcohol, a buffer, an amino acid, and/or a surfactant. In one embodiment, the particles comprise V-R-G active agent and <6% water (w/w). In one embodiment, the water is <3% (w/w).

In one embodiment, the shape of some or each particle(s) are/is approximately spheroidal. In another embodiment, the shape of some or each particle(s) are/is approximately cylindrical. In one embodiment, the aspect ratio of the particle is >0.40, >0.50, >0.60, >0.70, >0.80, or >0.90. In another embodiment, the aspect ratio of the particle is about 0.90 to about 0.98. The shape of the particle may be determined inter alia by micro-flow imaging (MFI).

In one embodiment, the mean diameter of the particle(s) is/are <50 microns. In one embodiment, the mean diameter of the particle(s) is/are <25 microns. In another embodiment, the mean diameter of the particle(s) is/are <10 microns. In yet another embodiment, the diameter of the particle(s) is/are about 0.05 microns to about 25 microns, about 0.1 microns to about 10 microns, about 0.5 microns to about 5 microns, about 1 micron, about 2 microns, about 3 microns, about 4 microns, or about 5 microns. Diameter may be determined inter alia, e.g., by micro-flow imaging (MFI) or static light scattering.

In some embodiments, the particle(s) comprise a small molecule excipient capable of assembling into a macromolecular assembly (SME). In one embodiment, the small molecule excipient is fumaryl diketopiperazine (FDKP.) In one embodiment, the SME is present at about one part SME per ten parts V-R-G active agent (1:10) by weight, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, or about 10:1 parts SME to V-R-G active agent by weight.

In some embodiments, the particle(s) also comprises a buffer, such as e.g., phosphate, histidine, and/or acetate. In one embodiment, the buffer is present at about 1% to 2% (w/w).

In some embodiments, the particle(s) also comprise a thermal stabilizer, which can be inter alia, e.g., a sugar, sugar alcohol, amino acid, and/or a combination thereof. Amino acids include inter alia alanine, isoleucine, proline, valine, leucine, and arginine. In one embodiment, the thermal stabilizer includes trehalose, mannitol, sucrose, and/or isoleucine. In a specific embodiment, the thermal stabilizer is mannitol. In another specific embodiment, the thermal stabilizer comprises mannitol or other sugar alcohol at about one part sugar alcohol per ten parts V-R-G active agent (1:10) by weight, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, or about 10:1 parts sugar alcohol to V-R-G active agent by weight.

In one embodiment, the particle(s) also comprises a surfactant. In one embodiment, the surfactant is an amphipathic nonionic surfactant, such as e.g., a fatty acid ester of a polyoxyethylene sorbitan. In one embodiment, the surfactant comprises polysorbate 20 or polysorbate 80, at about 0.015-1-part polysorbate per five (5) parts Verteporfin by weight. In certain specific embodiments, the polysorbate 20 or polysorbate 80 is present at about 0.15, 0.3, 0.6, 1, 1.5, 3, 6, or 10 parts of polysorbate per 50 parts V-R-G active agent by weight.

Verteporfin has a serum half-life of about 5-6 hours, but the tumor half-life is envisioned to be longer at about 24 hours or more in tumors, since fluorescence at 689 nm (excitation 405 nm) is seen in tumors up to 24 hours after Verteporfin intravenous delivery. Verteporfin's extent of exposure and maximal plasma concentration are proportional to the dose between 6-20 mg/m$^2$ (label for retinal age related macular degeneration is 6 mg/m$^2$, but at 0.3 mg/kg in a recent clinical trial). Thus, in one embodiment, a cancer is treated by administering daily dose of DPI Verteporfin (or V-R-G active agent), which may be used by patient at home. This provides a distinct advantage to intravenous dosing, which often requires supervised care at infusion center, hospital, or the like.

The reason for daily administration of Verteporfin is because it has been demonstrated that Verteporfin inhibits YAP1 and inhibiting YAP1 has been shown to decrease PD-L1 and EGFR, which are both important anti-cancer targets. DPI Verteporfin (or V-R-G active agent) is envisioned to be more effective than the standard large and hydrophilic monoclonal medicaments due to its ability to penetrate the dense tumor microenvironment to get to the target tumor.

Thus, in one embodiment, the DPI Verteporfin (or Verteporfin-containing embodiments of the V-R-G active agent) formulation is administered to a patient in need for treating any tumor that is YAP1 positive (for example lung, pancreas, bladder, liver, breast, brain, gastric, and the like) or PD-L1 positive (and possibly EGFR and EGFR resistant T790M positive) tumors.

In another embodiment, dry-powder Verteporfin (or Verteporfin-containing embodiments of the V-R-G active agent) delivered via airway is used for imaging (fluorescence emission at 689 nm after excitation at 405 nm), photodynamic therapy, Cherenkov radiation induced PDT via PET scan or standard radiation, and retina and choroid laser treatment.

The invention provides several formulations, treatment regimens, and routes of administration of the V-R-G active agent, including oral administration, topical administration, intraperitoneal administration, intravesical administration, intravenous administration, subcutaneous, intramuscular, and the like, in addition to the pulmonary deposition modes (e.g., inhaled dry powder, inhaled aerosols, and the like).

In one aspect, the invention provides an oral dosed liposomal Verteporfin for use in treating pancreatic cancer, esophageal, gastric, colon, and other gastrointestinal cancers, dysplasias, neoplasias, or hyperplasias, such as for example Barrett's esophagus, head and neck cancer, lung cancer, and non-cancer-oral leukoplakia.

In another aspect, the invention provides a liquid dosed Verteporfin solution or emulsion for use in the treating non-muscle bladder cancer by direct instillation into the bladder.

In another aspect, the invention provides a solid dry powder form or aerosol form of Verteporfin for use in treating primary and metastatic lung cancer, interstitial pulmonary fibrosis, skin cancer, non-cancer skin conditions such as psoriasis, and other gastrointestinal cancers, dysplasias, neoplasias, or hyperplasias.

In one embodiment, the Verteporfin is a dry powder that can be administered with a dry powder inhaler, such as, e.g., a breath-powered single-use or reusable inhaler. See U.S. Pat. Nos. 7,464,706B2, 846,588B2, WO2009121020A1, US20170216538A1 US20180228987A1, U.S. Pat. No. 9,700,690B2, U.S. D635,241S1, WO2014144895A1, and U.S. D605,753S1 for descriptions of exemplar breath-powered inhaler devices.

In another embodiment, the Verteporfin is an aerosolized liquid or vaper containing emulsified or solubilized Verteporfin that can be administered inter alia via a nebulizer, a pressurized metered-dose inhaler, or the like.

In another aspect, the invention provides a liquid or gel Verteporfin liposomal or stable emulsion formula for use as a topical medicament for treating skin conditions such as skin-non-melanoma, melanoma and chronic skin conditions such as, e.g., psoriasis.

In another aspect, the invention provides a pharmaceutical formulation containing a Verteporfin formulation of any one or more of the previous described aspects combined with another medicament or excipient. In one embodiment, the other medicament is an anti-cancer drug. In a specific embodiment, the other medicament is Gemcitabine. In another embodiment, the other medicament or excipient is one or more of a sugar alcohol, such as, e.g., mannitol, and a self-assembling molecule, such as, e.g., fumaryl diketopiperazine. In another embodiment, the other medicament or excipient includes one or more bronchospasm prevention medicaments, such as, e.g., ipratropium bromide and albuterol sulfate.

In another aspect, the invention provides a method of treating a disease containing the step of contacting a tissue of a patient in need with a pharmaceutical formulation of any one or more of the other aspects described. In one embodiment, the tissue is a respiratory system mucosa, including alveoli. In another embodiment, the tissue is a tumor. In some embodiments, the Verteporfin-containing pharmaceutical formulation is combined with another medicament. In another embodiment, another medicament is administered to the patient before, during, or after administration of the Verteporfin-containing pharmaceutical formulation. In a specific embodiment, the other medicament is Gemcitabine.

In another aspect, the invention provides a method of treating a disease containing the step of contacting a tissue of a patient in need with a pharmaceutical formulation of any one or more of the other aspects followed by administering radiation to a diseased tissue in the patient, which may or may not be the tissue to which the formulation is initially contacted. In one embodiment, the tissue is a respiratory system mucosa, including alveoli. In another embodiment, the tissue is a tumor. In another embodiment, the diseased tissue is a tumor. In some embodiments, the Verteporfin-containing pharmaceutical formulation is combined with another medicament. In another embodiment, another medicament is administered to the patient before, during, or after administration of the Verteporfin-containing pharmaceutical formulation, followed by administering radiation. In a specific embodiment, the other medicament is Gemcitabine. In one embodiment, the patient or formulation is supplemented with $O_2$.

In another aspect, the invention provides any one or more of the Verteporfin-containing, Gemcitabine-containing, N-acetylcysteine-containing, or Ribavirin-containing formulations of any other aspect combined perfluorocarbon or perfluorocarbon emulsions and with other drugs for therapeutic, diagnostic, or theranostic purposes.

In another aspect, the invention provides a solid dry powder form or aerosol form of Ribavirin for use in treating lung infection or pneumonia, especially a viral lung infection such as, e.g., coronavirus or influenza virus.

In one embodiment, the Ribavirin is in a dry powder that can be administered with a dry powder inhaler, such as, e.g., a breath-powered single-use or reusable inhaler. See U.S. Pat. Nos. 7,464,706B2, 8,465,88B2, WO2009121020A1, US20170216538A1 US20180228987A1, U.S. Pat. No. 9,700,690B2, U.S. D635241S1, WO2014144895A1, and U.S. D605753S1 for descriptions of exemplar breath-powered inhaler devices.

In another embodiment, the Ribavirin is an aerosolized liquid or vaper containing emulsified or solubilized Ribavirin that can be administered inter alia via a nebulizer, a pressurized metered-dose inhaler, or the like.

In another aspect, the invention provides a pharmaceutical formulation containing a Ribavirin formulation of the previous aspect combined with another medicament or excipient. In one embodiment, the other medicament or excipient is a perfluorocarbon, such as, e.g., perflubron. In another embodiment, the other medicament or excipient is one or more of a sugar alcohol, such as, e.g., mannitol, and a self-assembling molecule, such as, e.g., fumaryl diketopiperazine.

In another aspect, the invention provides a solid dry powder form or aerosol form of N-acetyl cysteine (NAC) for use in treating lung infection, pneumonia, or acute respiratory distress syndrome, COPD, or the like.

In one embodiment, the NAC is in a dry powder that can be administered with a dry powder inhaler, such as, e.g., a breath-powered single-use or reusable inhaler. See U.S. Pat. Nos. 7,464,706B2, 8,146,588B2, WO2009121020A1, US20170216538A1 US20180228987A1, U.S. Pat. No. 9,700,690B2, U.S. D635241S1, WO2014144895A1, and U.S. D605753S1 for descriptions of exemplar breath-powered inhaler devices.

In another embodiment, the NAC is an aerosolized liquid or vaper containing emulsified or solubilized NAC that can be administered inter alia via a nebulizer, a pressurized metered-dose inhaler, or the like.

In another aspect, the invention provides a pharmaceutical formulation containing a NAC formulation of the previous aspect combined with another medicament or excipient. In one embodiment, the other medicament or excipient is a perfluorocarbon, such as, e.g., perflubron. In another embodiment, the other medicament or excipient is one or more of a sugar alcohol, such as, e.g., mannitol, and a self-assembling molecule, such as, e.g., fumaryl diketopiperazine. In another embodiment, the other medicament or excipient includes one or more bronchospasm prevention medicaments, such as, e.g., ipratropium bromide and albuterol sulfate.

In another aspect, the invention provides a solid dry powder form or aerosol form of high molecular weight hyaluronan (HMW-H) for use in treating patients at risk for acute respiratory distress syndrome.

In one embodiment, the HMW-H is in a dry powder that can be administered with a dry powder inhaler, such as, e.g., a breath-powered single-use or reusable inhaler. See U.S. Pat. Nos. 7,464,706B2, 8,146,588B2, WO2009121020A1, US20170216538A1 US20180228987A1, U.S. Pat. No. 9,700,690B2, U.S. D635241S1, WO2014144895A1, and U.S. D605753S1 for descriptions of exemplar breath-powered inhaler devices.

In another embodiment, the HMW-H is an aerosolized liquid or vaper containing emulsified or solubilized HMW-H that can be administered inter alia via a nebulizer, a pressurized metered-dose inhaler, or the like.

In another aspect, the invention provides a pharmaceutical formulation containing a HMW-H formulation of a previous aspect combined with another medicament or excipient. In one embodiment, the other medicament or excipient is a perfluorocarbon, such as, e.g., perflubron. In another embodiment, the other medicament or excipient is one or more of a sugar alcohol, such as, e.g., mannitol, and a self-assembling molecule, such as, e.g., fumaryl diketopiperazine. In another embodiment, the other medicament or excipient includes one or more bronchospasm prevention medicaments, such as, e.g., ipratropium bromide and albuterol sulfate.

In another aspect, the invention provides an oral dosed liposomal Gemcitabine for use in treating pancreatic cancer, esophageal, gastric, colon, and other gastrointestinal cancers, lung cancers, head and neck cancer, non-cancer-oral leukoplakia, dysplasias, neoplasias, or hyperplasias, such as for example Barrett's esophagus.

In another aspect, the invention provides a liquid dosed Gemcitabine solution or emulsion for use in the treating non-muscle bladder cancer by direct instillation into the bladder. In one embodiment this would be combined with perfluorocarbon such as Perflubron and Verteporfin.

In another aspect, the invention provides a solid dry powder form or aerosol form of Gemcitabine for use in treating primary and metastatic lung cancer, interstitial pulmonary fibrosis, skin cancer, non-cancer skin conditions such as psoriasis, and other gastrointestinal cancers, dysplasias, neoplasias, or hyperplasias.

In one embodiment, the Gemcitabine is a dry powder that can be administered with a dry powder inhaler, such as, e.g., a breath-powered single-use or reusable inhaler. See U.S. Pat. Nos. 7,464,706B2, 8,146,588B2, WO2009121020A1, US20170216538A1 US20180228987A1, U.S. Pat. No. 9,700,690B2, U.S. D635241S1, WO2014144895A1, and U.S. D605753S1 for descriptions of exemplar breath-powered inhaler devices.

In another embodiment, the Gemcitabine is an aerosolized liquid or vaper containing emulsified or solubilized Gemcitabine that can be administered inter alia via a nebulizer, a pressurized metered-dose inhaler, or the like.

In another aspect, the invention provides a liquid or gel Gemcitabine liposomal or stable emulsion formula for use as a topical medicament for treating skin conditions such as skin-non-melanoma, melanoma and chronic skin conditions such as, e.g., psoriasis. In one embodiment oxygenated Perflubron and Verteporfin are added.

In another aspect, the invention provides a pharmaceutical formulation containing a Gemcitabine formulation of any one or more of a previous aspect combined with another medicament or excipient. In one embodiment, the other medicament is an anti-cancer drug. In a specific embodiment, the other medicament is Verteporfin. In one embodiment, the other medicament or excipient is a perfluorocarbon, such as, e.g., Perflubron. In another embodiment, the other medicament or excipient is one or more of a sugar alcohol, such as, e.g., mannitol, and a self-assembling molecule, such as, e.g., fumaryl diketopiperazine. In another embodiment, the other medicament or excipient includes one or more bronchospasm prevention medicaments, such as, e.g., ipratropium bromide and albuterol sulfate.

In yet another aspect, the invention provides an oral dosed liposomal Verteporfin, Ribavirin and Gemcitabine formulation for use in treating pancreatic cancer, esophageal, gastric, colon, and other gastrointestinal cancers, dysplasia's, neoplasia's, or hyperplasia's, such as for example Barrett's esophagus, head and neck cancer, and non-cancer-oral leukoplakia. Perflubron may also be used in combination or sequentially. In a second aspect, the invention provides a liquid dosed Verteporfin, Ribavirin and Gemcitabine solution or emulsion for use in the treating non-muscle bladder cancer by direct instillation into the bladder. Perflubron can be added sequentially or combined.

In another aspect, the invention provides a solid dry powder inhaler form or nebulized aerosol form of Verteporfin, Ribavirin, and Gemcitabine for use in treating primary and metastatic lung cancer, interstitial pulmonary fibrosis, skin cancer and non-cancer skin conditions such as psoriasis (spray treatment), and other gastrointestinal cancers, dysplasias, neoplasias, or hyperplasias.

In one embodiment, the Verteporfin, Ribavirin, and Gemcitabine is a dry powder formulation that can be administered with a dry powder inhaler, such as, e.g., a breath-powered single-use or reusable inhaler. See U.S. Pat. Nos. 7,464,706B2, 8,146,588B2, WO2009121020A1, US20170216538A1 US20180228987A1, U.S. Pat. No. 9,700,690B2, U.S. D635241S1, WO2014144895A1, and U.S. D605753S1 for descriptions of exemplar breath-powered inhaler devices.

In another embodiment, the Verteporfin, Ribavirin, and Gemcitabine is an aerosolized liquid or vaper formulation containing emulsified or solubilized Verteporfin that can be administered inter alia via a nebulizer, a pressurized metered-dose inhaler, or the like.

In another aspect, the invention provides a liquid or gel Verteporfin, Ribavirin, and Gemcitabine liposomal or stable emulsion formula for use as a topical medicament for treating skin conditions such as skin-non-melanoma, melanoma and chronic skin conditions such as, e.g., psoriasis. In one embodiment perflubron will be added.

In another aspect, the invention provides a pharmaceutical formulation containing a Verteporfin, Ribavirin, and Gemcitabine formulation of any one or more of the previous V-R-G active agent-containing aspects combined with another medicament or excipient. In one embodiment, the other medicament is an anti-cancer drug. In a specific embodiment, the other medicament is a tyrosine kinase inhibitor e.g. nintedanib. In another embodiment, the other medicament or excipient is one or more of a sugar alcohols, such as, e.g., mannitol, and a self-assembling molecule, such as, e.g., fumaryl diketopiperazine. In another embodiment, the other medicament or excipient includes one or more bronchospasm prevention medicaments, such as, e.g., ipratropium bromide and albuterol sulfate.

In another aspect, the invention provides a method of treating a disease containing the step of contacting a tissue of a patient in need with a pharmaceutical formulation of any one or more of the V-R-G active agent-containing aspects. In one embodiment, the tissue is a respiratory system mucosa, including alveoli. In another embodiment, the tissue is a tumor. In some embodiments, the Verteporfin, Ribavirin, and Gemcitabine containing pharmaceutical formulation is combined with another medicament. In another embodiment, another medicament is administered to the patient before, during, or after administration of the Verteporfin, Ribavirin, and Gemcitabine-containing pharmaceutical formulation.

In another aspect, the invention provides a method of treating a disease containing the step of contacting a tissue of a patient in need with a pharmaceutical formulation of any one or more of the previous V-R-G active agent-containing aspects followed by administering radiation to a diseased tissue in the patient, which may or may not be the tissue to which the formulation is initially contacted. In one embodiment, the tissue is a respiratory system mucosa, including alveoli. In another embodiment, the tissue is a tumor. In another embodiment, the diseased tissue is a tumor. In some embodiments, the Verteporfin, Ribavirin, and Gemcitabine-containing pharmaceutical formulation is combined with another medicament. In another embodiment, another medicament is administered to the patient before, during, or after administration of the Verteporfin, Ribavirin, and Gemcitabine-containing pharmaceutical formulation, followed by administering conventional or PET scan induced aka Cerenkov radiation or PDT or SDT. In one embodiment, the patient or formulation is supplemented with $O_2$.

In another aspect, the invention provides combining the Verteporfin, Ribavirin, and Gemcitabine drug combination with perfluorocarbon or perfluorocarbon emulsions and with other drugs for therapeutic, diagnostic, or theragnostic purposes.

In another aspect, the invention provides a solid dry powder form or aerosol form of combined Verteporfin, Ribavirin, and Gemcitabine for use with or without perflubron in treating lung infection or pneumonia, especially a viral lung infection, preferably SARS CoV-2 coronavirus or influenza virus.

In one embodiment, the combined Verteporfin, Ribavirin, and Gemcitabine is in a dry powder form that can be administered with a dry powder inhaler, such as, e.g., a breath-powered single-use or reusable inhaler. See U.S. Pat. Nos. 7,464,706B2, 8,146,588B2, WO2009121020A1, US20170216538A1 US20180228987A1, U.S. Pat. No. 9,700,690B2, U.S. D635241S1, WO2014144895A1, and U.S. D605753S1 for descriptions of exemplar breath-powered inhaler devices.

In another embodiment, the combined Verteporfin, Ribavirin, and Gemcitabine is an aerosolized liquid or vapor containing emulsified or solubilized Ribavirin that can be administered inter alia via a nebulizer, a pressurized metered-dose inhaler, or the like.

In another aspect, the invention provides a pharmaceutical formulation containing a combined Verteporfin, Ribavirin, and Gemcitabine formulation of the previous aspect combined with another medicament or excipient. In one embodiment, the other medicament or excipient is a perfluorocarbon, such as, e.g., perflubron. In another embodiment, the other medicament or excipient is one or more of a sugar alcohol, such as, e.g., mannitol, and a self-assembling molecule, such as, e.g., fumaryl diketopiperazine.

In another aspect, the invention provides Verteporfin, Ribavirin, and Gemcitabine plus a solid dry powder form or aerosol form of N-acetyl cysteine (NAC) for use in treating post lung infection specifically SARS coV-2, pneumonia, or acute respiratory distress syndrome, COPD, or the like.

In one embodiment, the NAC is in a dry powder that can be administered with a dry powder inhaler, such as, e.g., a breath-powered single-use or reusable inhaler. See U.S. Pat. Nos. 7,464,706B2, 8,146,588B2, WO2009121020A1, US20170216538A1 US20180228987A1, U.S. Pat. No. 9,700,690B2, U.S. D635241S1, WO2014144895A1, and U.S. D605753S1 for descriptions of exemplar breath-powered inhaler devices.

In another embodiment, the NAC is an aerosolized liquid or vapor containing emulsified or solubilized NAC that can be administered inter alia via a nebulizer, a pressurized metered-dose inhaler, or the like.

In another aspect, the invention provides a pharmaceutical formulation containing a NAC formulation of the previous aspect combined with another medicament or excipient. In one embodiment, the other medicament or excipient is a perfluorocarbon, such as, e.g., perflubron. In another embodiment, the other medicament or excipient is one or more of a sugar alcohol, such as, e.g., mannitol, and a self-assembling molecule, such as, e.g., fumaryl diketopiperazine. In another embodiment, the other medicament or excipient includes one or more bronchospasm prevention medicaments, such as, e.g., ipratropium bromide and albuterol sulfate.

In another aspect, the invention provides Verteporfin, Ribavirin, and Gemcitabine in a solid dry powder form or aerosol form plus high molecular weight hyaluronan (HMW-H) for use in treating patients at risk for acute respiratory distress syndrome.

In one embodiment, the HMW-H is in a dry powder that can be administered with a dry powder inhaler, such as, e.g., a breath-powered single-use or reusable inhaler. See U.S. Pat. Nos. 7,464,706B2, 8,146,588B2, WO2009121020A1, US20170216538A1 US20180228987A1, U.S. Pat. No. 9,700,690B2, U.S. D635241S1, WO201444895A1, and U.S. D605753S1 for descriptions of exemplar breath-powered inhaler devices.

In another embodiment, the HMW-H is an aerosolized liquid or vapor containing emulsified or solubilized HMW-H that can be administered inter alia via a nebulizer, a pressurized metered-dose inhaler, or the like.

In another aspect, the invention provides a pharmaceutical formulation containing a HMW-H formulation of a previous aspect combined with another medicament or excipient. In one embodiment, the other medicament or excipient is a perfluorocarbon, such as, e.g., Perflubron. In another embodiment, the other medicament or excipient is one or more of a sugar alcohol, such as, e.g., mannitol, and a self-assembling molecule, such as, e.g., fumaryl diketopiperazine. In another embodiment, the other medicament or excipient includes one or more bronchospasm prevention medicaments, such as, e.g., ipratropium bromide and albuterol sulfate.

While not wishing to be bound by theory, as both Verteporfin and Gemcitabine are radiosensitizers and the administration of radiation to the disease tissue is expected to generate Cherenkov radiation at the site of diseased tissue and formulation, thereby enabling photodynamic therapy (PDT) along with conventional radiation effects to treat the diseased tissue (Wang et al., "X-Ray Induced Photodynamic Therapy: A Combination of Radiotherapy and Photodynamic Therapy," Theranostics, 30 Sep. 2016, 6(13):2295-2305) In addition SDT is contemplated.

The loading of Verteporfin also enables inhibition of ABCG2, which is generally known as a substrate for Gemcitabine and involved in efflux of Gemcitabine, thereby improving the efficacy of Gemcitabine. The convenience of DPI allows the Verteporfin, Ribavirin and Gemcitabine to be given at home and at less expense than intravenous administration. Other advantages of frequent DPI of Verteporfin (e.g. daily or several times per cycle) include the possible control of side populations of lung cancer stem cells as well as decreasing PD-L1 expression by cancer and other tumor cells (Hsu et al. "Inhibition of yes-associated protein downregulates PD-L1 (CD274) expression in human malignant pleural mesothelioma," Journal of Cellular and Molecular Medicine, 2018 June, 22(6): 3139-3148; Yi et al., "YAP1 regulates ABCG2 and cancer cell side population in human lung cancer cells," Oncotarget, 2017 Jan. 17, 8(3): 4096-4109). While not wishing to be bound by theory, Verteporfin is expected to have greater anti-PD-L1 activity compared to approved monoclonal antibodies, which are large and hydrophobic, due to the liposomal hydrophobicity and small size of Verteporfin, and direct airway delivery which enables better penetration deeply into the tumor.

Also, DPI of Verteporfin is expected to enable imaging and confirm biopsy of target tissue using both in vivo (CELLVIZIO) and ex vivo methods (LICOR PEARL IMAGING) and photodynamic therapy that can be delivered by local laser but possibly by external beam radiation or even PET, PDT or SDT energy.

Verteporfin is also expected to have an impact without light including reduced YAP1 and consequent decreased tumor growth, improved immune response by reduced PD-L1 expression, decreased efflux of drugs out of tumor, and by binding lipoproteins and consequent enhanced uptake by highly expressed LDL receptors on cancer cells, especially pancreatic cancer.

Additional advantages of an inhaled DPI Verteporfin over intravenous for lung or other cancers may include, for example, 1) easier delivery of frequent doses of Verteporfin, 2) the pulmonary route delivery can be performed from home without specialized services such as a hospital or even home health RN, 3) daily Verteporfin may allow a durable anti-YAP1 effect (reduce YAP1 translocation to nucleus) and other, e.g., pancreatic, cancer inhibition, e.g., by reducing expression of PD-L1 and ABCG2, and 4) the more protracted DPI delivery as opposed to current label venous bolus may increase overall tumor uptake of the same total Verteporfin dose.

DPI Verteporfin efficacy may occur by introduction of Verteporfin, Ribavirin and Gemcitabine into pulmonary circulation then into systemic arterial system including, e.g., the pancreatic cancer arteries as opposed to the initial traditional venous entry whereby a bolus of drug may be lost prior to cardiac output. This may prove advantageous and enable an overall lower Verteporfin dose and reduced adverse events.

EXAMPLES

Example 1: Treating Lung Cancer

A 56 year old former smoker with Stage 3b lung cancer and who has progressed, receives Verteporfin via dry powder inhalation (DPI) 30 mg daily for 3 days prior to each intravenous Gemcitabine dosing on Days 1, 8 and 15 on a 28 day cycle The patient has local radiation 24 hours after each Gemcitabine administration with supplemental $O_2$ to complete the initial therapy. Since as both Verteporfin and Gemcitabine are radiosensitizers, photodynamic therapy (PDT) via Cherenkov radiation e.g., PET induced along with conventional radiation effects is expected. Alternatively, combined Verteporfin, Ribavirin and Gemcitabine is given by dpi for the lung cancer patient plus photodynamic therapy (PDT) or sonodynamic therapy (SDT) with excitation of Verteporfin. Perflubron is instilled in the designated airway to reduce scatter.

Example 2: Pancreatic Cancer

A 60-year-old former smoker and reformed alcoholic develops severe abdominal pain and stage 4 pancreatic cancer diagnosed by Endoscopic Ultrasound (EUS). A subsequent EUS delivers 7 mL of liposomal Gemcitabine or Verteporfin at 2.5 mg/ml containing oxygenated Perflubron prior to and during PDT/SDT. Pre and post pancreatic EUS Elastography is used to determine the impact of the directly injected liposomal Gemcitabine or Verteporfin Perflubron formulation for PDT/SDT on stroma. Also pre and post needle probe confocal laser endomicroscopy is utilized with CELLVIZIO 488/660 nm excitation (400 nm ex preferred if available), or modification thereof, assisted with post liposomal Verteporfin, which allows a qualitative and possible quantitative estimate of Gemcitabine or Verteporfin delivery in vivo, followed by biopsy and ex vivo evaluation under LICOR PEARL TRIOLOGY and ODYSSEY IMAGING. Photodynamic or sonodynamic therapy may occur anytime from 1-20 minutes post injection to 48 hours later at subsequent procedure. The applied injection is expected to be 0.5-10 mL direct intratumoral injection under EUS and may combine with additional intratumoral or intravenous Gemcitabine and/or other standard of care modalities. Other specific unique method applications for this include Raman spectroscopy needle to localize Perflubron and CT/PET and radiotherapy to induce Cherenkov radiation for PDT. Intravenous and DPI may be used together as in lung cancer. Combined intravenous and direct injection and followed by DPI for daily delivery may be administered.

Example 3: Atherosclerosis

A 65-year-old male who lives in a rural area and had a drug-eluting stent placed in his left anterior descending artery (LAD) 5 years ago. He has required multiple procedures for re-stenosis of his LAD stent and has a history of peripheral arterial stenosis of his right lower extremity and who is now being planned for a novel photodynamic therapy by cardiac (radial artery approach) and right femoral artery catheterization. The patient is prepped by inhaling Verteporfin DPI 30 mg ter in die (TID) for 2 days prior to the procedure to load atherosclerotic plaque prior to vascular approach of PDT (see, e.g., Jain et al., "Intra-Arterial Drug and Light Delivery for Photodynamic Therapy Using Visudyne®: Implication for Atherosclerotic Plaque Treatment," Frontiers in Physiology, September 2016, 7(400): 1-13). The Verteporfin DPI protracted delivery is expected to yield more Verteporfin uptake into the plaque than the bolus intravenous route and at a lower dose. Fluorescent imaging is employed to locate the stent and native atherosclerotic obstruction. Intravenous oxygenated Perflubron emulsion administration and subsequent or coincident SDT may also be employed.

Example 4: Navigational Biopsy Confirmation of Target by Ex Vivo Imaging and PDT/SDT A 72-year-old smoker with severe COPD (FEV1 25% predicted DLCO 30%) is undergoing navigational bronchoscopy for a 2 cm distal right lower lobe mass suspicious of lung cancer. The patient is given Verteporfin DPI 30 mg quater in die (QID) the day prior to bronchoscopy. The patient is sedated, and biopsy of the lung mass proceeded, and positive tissue is obtained and confirmed using an ex vivo imaging instrument (e.g., LICOR PEARL IMPULSE imaging system, LI-COR Biosciences, Lincoln, Nebr.). The third biopsy specimen taken is confirmed to be fluorescent bright at 689 nm and is positive on probe-based confocal laser endoscopy (pCLE) viewed by pathology (here, the other two were negative). Photodynamic therapy or sonodynamic therapy ("PDT/SDT") is performed. While intravenous Verteporfin enables imaging of the lung cancer, the administering of Verteporfin DPI the day prior to admission is far less expensive and far more convenient. The patient is considered inoperable, therefore PDT/SDT is performed and is much better tolerated than would be expected than stereotactic radiation and at a much reduced cost. Instilled Perflubron will allow reduced levels of light (PDT) and sound (SDT) to be needed for efficacy. An endobronchial ultrasound (EBUS)-like instrument maybe used for administering therapeutic sound waves (SDT).

Intravenous Verteporfin may be used concurrently with Verteporfin DPI. The Verteporfin DPI can be given the day before from home to load the tumor parenchyma and lymph nodes, then, on day of EBUS-guided photodynamic therapy (or another technique to excite the Verteporfin molecule), an intravenous dose is administered, and PDT/SDT is performed 10-15 minutes after administration, thereby enabling both vasculature and tumor parenchymal killing by PDT. Verteporfin is expected to be loaded into tumor parenchyma when dosed many hours before PDT/SDT, whereas intravenous Verteporfin would be expected to be mainly located within the tumor vasculature at 10-30 minutes after dosing. (See He et al., "Hypoxia regulates ABCG2 activity through the activation of ERK1/2/HIF-1a and contributes to chemoresistance in pancreatic cancer cells," CANCER BIOLOGY & THERAPY 2016, VOL. 17, NO. 2, 188-198.)

Example 5: Bladder Cancer—Non-Muscle

An 80-year-old white male former smoker who presented with hematuria is found to have a mass on office cystoscopy. A Stage 1b bladder cancer is suspected and confirming biopsy is performed. At a pre-trans urethral resection of bladder tumor (TURBT) office visit, a liposomal Verteporfin 30 mg in 100 ml 5% dextrose-in-water ($D_5W$) is administered and held for 1 hour, and the patient is scheduled for TURBT either the same day or the next day. At cystoscopy, a Karl Storz 400 nm excitation light identifies the red 689 nm light emitted from the Verteporfin. Resection is performed for the bulk of the cancer followed by "clean up" PDT (i.e., PDT following gross resection). Verteporfin is more concentrated into the tumor as opposed to nonspecifically in muscle tissue at 24 hours, but also specifically "kills" the appropriate cancer and cancer-associated cells in muscle. SDT may be added or utilized alone after Verteporfin tumor loading.

Given its relatively small molecular weight and relative hydrophobicity, Verteporfin penetrates deeper than current photosensitizers. Also, Verteporfin may be dosed daily for 1 week following initial treatment via straight catheterization, where the Verteporfin has intrinsic anti-bladder cancer effects and may keep cancer stem cells from being rescued. (See, e.g., Dong et al., "Verteporfin inhibits YAP-induced bladder cancer cell growth and invasion via Hippo signaling pathway," International Journal of Medical Sciences, 2018, 15(6): 645-652).

Here also, administering Verteporfin, Ribavirin, and Gemcitabine by dry powder inhalation (DPI) could be used for metastatic bladder treatment.

Example 6: Barrett's Esophagus and PDT

A 58-year-old male with history severe gastrointestinal reflux disease is found to have significant intestinal metaplasia on endoscopy and treatment with PDT/SDT is planned. The patient is given an oral dose of liposomal Verteporfin 30 mg 24 hours and 15 mg by i.v. 1 hour before planned treatment using PDT/SDT via endoscopy. The i.v. dose enables visualization, then PDT at 689 nm is performed. Since Verteporfin is excited at 405 nm, photodynamic diagnosis may be utilized until quenching occurs, which reduces overall total light dosing. Here also, SDT could be used alone or concurrently.

Example 7: Coronavirus Infection

A 67-year-old female nonsmoker having no previous lung disease develops symptoms of fever for 2 days and is then immediately started on Ribavirin dpi 2 p or 60 mg twice daily for 6 days. The patient subsequently shows symptomatic improvement. She avoids hospitalization and thereby avoids what may have been up to an increased 15-20% risk. Verteporfin and Gemcitabine dpi could be substituted for the Ribavirin.

Example 8: COPD and Bilateral Pneumonia

A 54-year-old male smoker with history of moderate chronic obstructive pulmonary disease (COPD) mixed type who has been diagnosed with acute respiratory distress syndrome (ARDS) secondary to bilateral pneumonia. The patient has a very productive cough but not expectorating significant secretions and is currently on high flow system 70% FIO2 (fraction of inspired oxygen). CT chest reveals bilateral infiltrates and mucus plugging of airways. The patient is initiated on acetylcysteine dpi every 4 hours along with a bronchodilator (e.g., DUONEB albuterol and ipratropium). The patient begins to expectorate sputum and can titrate O₂ and avoid mechanical ventilation.

Example 9: Lung Metastasis

A 17-year-old female high school soccer player who noted left lower leg pain for 2 months initially thought to be musculoskeletal pain from soccer but ultimately imaging revealed a 4 cm mass that was resected and she was found to have osteosarcoma. 2 months later, after standard chemo-radiotherapy is completed, she is found to have three 1-cm lung metastases. She undergoes second line treatment but the lesions progress, so she is started on Gemcitabine 60 dpi BID and has stabilization for 12 months thereafter. Here also, Verteporfin, Ribavirin, and/or Gemcitabine dpi could all be given together coupled with inhaled or intravenous Perflubron (emulsion).

Example 10: Lung Bilateral Infiltrates and Risk for ARDS

A 50-year-old male smoker has a motor vehicle accident with chest abdomen and pelvis fractures and presents with bilateral infiltrates. The patient is at high risk for ARDS and so is immediately initiated on DPI high molecular weight hyaluronan (HWM-H) every 4 hours and is thereafter able to be maintained on high flow nasal cannula at 6 liters per minute (1 pm) and avoids mechanical ventilation. Perflubron by meter dosed inhaler 4 p QID can also be used alone or in combination.

Example 11: Interstitial Pulmonary Fibrosis

A 62 year old nonsmoker farmer has a diagnosis of interstitial pulmonary fibrosis with progressive symptoms over the past 6 months and with reduction in FVC by Pulmonary Function testing. The patient is initiated on Verteporfin 15 mg 1 p BID, which has a stabilizing effect on lung decline likely due to inhibition of myofibroblasts. Here also, Verteporfin combined with inhaled Perflubron nintedanib may be given. Subsequent or concomitant PDT and/or SDT promotes the elimination of myofibroblasts/macrophages that are otherwise engaged in fibrosis.

While the present invention has been illustrated by description of various embodiments and while those embodiments have been described in considerable detail, it is not the intention of applicant to restrict or in any way limit the scope of the appended claims to such details. Additional advantages and modifications will readily appear to those skilled in the art. The invention in its broader aspects is therefore not limited to the specific details and illustrative examples shown and described. Accordingly, departures may be made from such details without departing from the spirit or scope of applicant's invention.

Example 12: Gioblastoma Multiforme

A 64-year-old white male, who initially developed headaches and a seizure, was found to have a mass in the right temporal region and underwent surgical biopsy, which revealed Glioblastoma multiforme. The patient had standard of care treatment that included surgical resection, radiation and chemotherapy, but then had recurrence and is not candidate for surgical curative intent.

Immunohistochemistry at the 2nd operation is positive for PD-L1 and the patient is started on Verteporfin 15 mg two puffs twice daily both nasal and oral for the next six weeks. The patient has overall reduction in tumor mass and is therefore continued on same. Here, drug delivery via intravenous route is avoided and possible direct brain delivery via nasal pathway is enabled. Here, systematic delivery of the drug by both nasal and oral inhalation is contemplated.

The invention claimed is:

1. A pharmaceutical composition for direct delivery to lungs, the composition consisting of:
   a. 0-4% (w/w) water;
   b. 1-99% of drugs consisting of verteporfin and gemcitabine;
   c. a perfluorocarbon; and
   d. an excipient,
   wherein said composition is a powder consisting of particles with a mean diameter of about 0.1 microns to about 5 microns.

2. The pharmaceutical composition of claim 1, wherein the excipient is selected from the group consisting of a sugar, an amino acid, a sugar alcohol, a haloalkrane, fumaryl diketopiperazine, an inorganic salt and a combination thereof.

3. The pharmaceutical composition of claim 1, wherein said drugs are present at a concentration of >50% (w/w) in the composition.

4. The pharmaceutical composition of claim 1, wherein the excipient is mannitol or a sugar alcohol other than mannitol at a ratio of about one part of the mannitol or the sugar alcohol other than mannitol per ten parts of said drugs by weight.

5. The pharmaceutical composition of claim 1, wherein said composition is a dry powder and is administered with a dry powder inhaler.

6. The pharmaceutical composition of claim 1, wherein the excipient is a surfactant.

7. The pharmaceutical composition of claim 6, wherein the surfactant is polysorbate 20 or polysorbate 80 present at a concentration of about 0.015-1 part polysorbate 20 or polysorbate 80 per five (5) parts of said drugs by weight.

8. The pharmaceutical composition of claim 1, wherein the lungs are infected with a coronavirus, a SARS-CoV2 virus, or an influenza virus.

9. A pharmaceutical composition for direct delivery to lungs, the composition consisting of:
   a. >10% (w/w) water;
   b. 10-90% of drugs consisting of verteporfin and gemcitabine;
   c. a perfluorocarbon; and
   d. an excipient,
   wherein said composition is an aerosolized liquid.

10. The pharmaceutical composition of claim 9, wherein the excipient is selected from the group consisting of a sugar, an amino acid, a sugar alcohol, a buffer, an inorganic salt and a combination thereof.

11. The pharmaceutical composition of claim 9, wherein said drugs are present in the composition at a concentration of >50% (w/w).

12. The pharmaceutical composition of claim 9, wherein said composition is administered with a nebulizer.

13. The pharmaceutical composition of claim 9, wherein the excipient is a surfactant.

14. The pharmaceutical composition of claim 13, wherein the surfactant is polysorbate 20 or polysorbate 80 present at a concentration of about 0.015-1 part polysorbate 20 or polysorbate 80 per five (5) parts of said drugs by weight.

15. The pharmaceutical composition of claim 9, wherein the lungs are infected with a coronavirus, a SARS-CoV2 virus, or an influenza virus.

16. A pharmaceutical composition consisting of:
a. >10% (w/w) water;
b. 10-90% of drugs consisting of gemcitabine, verteporfin and ribavirin;
c. a perfluorocarbon; and
d. an excipient.

\* \* \* \* \*